US00PP28164P3

(12) United States Plant Patent
Randag

(10) Patent No.: US PP28,164 P3
(45) Date of Patent: Jul. 4, 2017

(54) VARIETY OF CALLA LILY PLANT NAMED 'ZAZU'

(50) Latin Name: *Zantedeschia sprengeri*
Varietal Denomination: Zazu

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 0 days.

(21) Appl. No.: 14/757,794

(22) Filed: Dec. 23, 2015

(65) Prior Publication Data

US 2016/0212917 P1 Jul. 21, 2016

Related U.S. Application Data

(60) Provisional application No. 62/125,226, filed on Jan. 15, 2015.

(51) Int. Cl.
*A01H 5/02* (2006.01)

(52) U.S. Cl.
USPC ..... Plt./490

(58) Field of Classification Search
USPC ..... Plt./490
CPC ..... A01H 5/0272
See application file for complete search history.

*Primary Examiner* — Kent L Bell
(74) *Attorney, Agent, or Firm* — The Webb Law Firm

(57) ABSTRACT

'Zazu' is a new variety of calla lily plant having inflorescences with a pink-colored spathe and a large throat spot that produces 4-25 inflorescences per tuber. The height of the top of an inflorescence above the soil can reach up to 45 cm, and the leaves are dark green with whitish spots and have a leathery texture.

2 Drawing Sheets

Botanical classification: *Zantedeschia sprengeri.*
Varietal denomination: 'ZAZU'.

BACKGROUND OF THE NEW PLANT

The present invention comprises a new and distinct cultivar of calla lily, botanically known as *Zantedeschia sprengeri* and hereinafter referred to by the cultivar name 'Zazu'.

'Zazu' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as C04005 (female parent, unpatented) with a *Zantedeschia sprengeri* selection referred to as C04011 (male parent, unpatented). 'Zazu' was selected in 2010 by the inventor in 't Zand, The Netherlands as one flowering plant within the progeny of the stated cross.

The first act of asexual reproduction of 'Zazu' by tissue culture was performed by the inventor in September of 2010 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 14 cm pots in 't Zand, The Netherlands under greenhouse conditions, which approximate those generally used in horticultural practice. Color references are made to The R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to basic characteristics of 'Zazu' which, in combination, distinguish this calla lily as a new and distinct cultivar:

1. Pink-colored spathe;
2. Large, dark purple throat spot from between Purple Group RHS N79A and 79C; and
3. High inflorescence production.

Further, when compared to calla lily plant named 'Samur' (unpatented), 'Samur' has an upper surface spathe color that varies between Red-Purple Group RHS 68B and 68D, whereas the upper surface spathe color of 'Zazu' varies between Red-Purple Group RHS 58D and 60A.

Table 1 provides similarities and differences of 'Zazu' to its parents, *Zantedeschia sprengeri* selections C04005 and C04011.

TABLE 1

| 'Zazu' | Similarities | Differences |
|---|---|---|
| C04005 | White spots on leaves | Spathe color<br>Number of inflorescences<br>Spathe shape |
| C04011 | Leaf shape<br>Plant height<br>Spathe shape | Leaf color<br>Spathe color<br>Spathe size |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
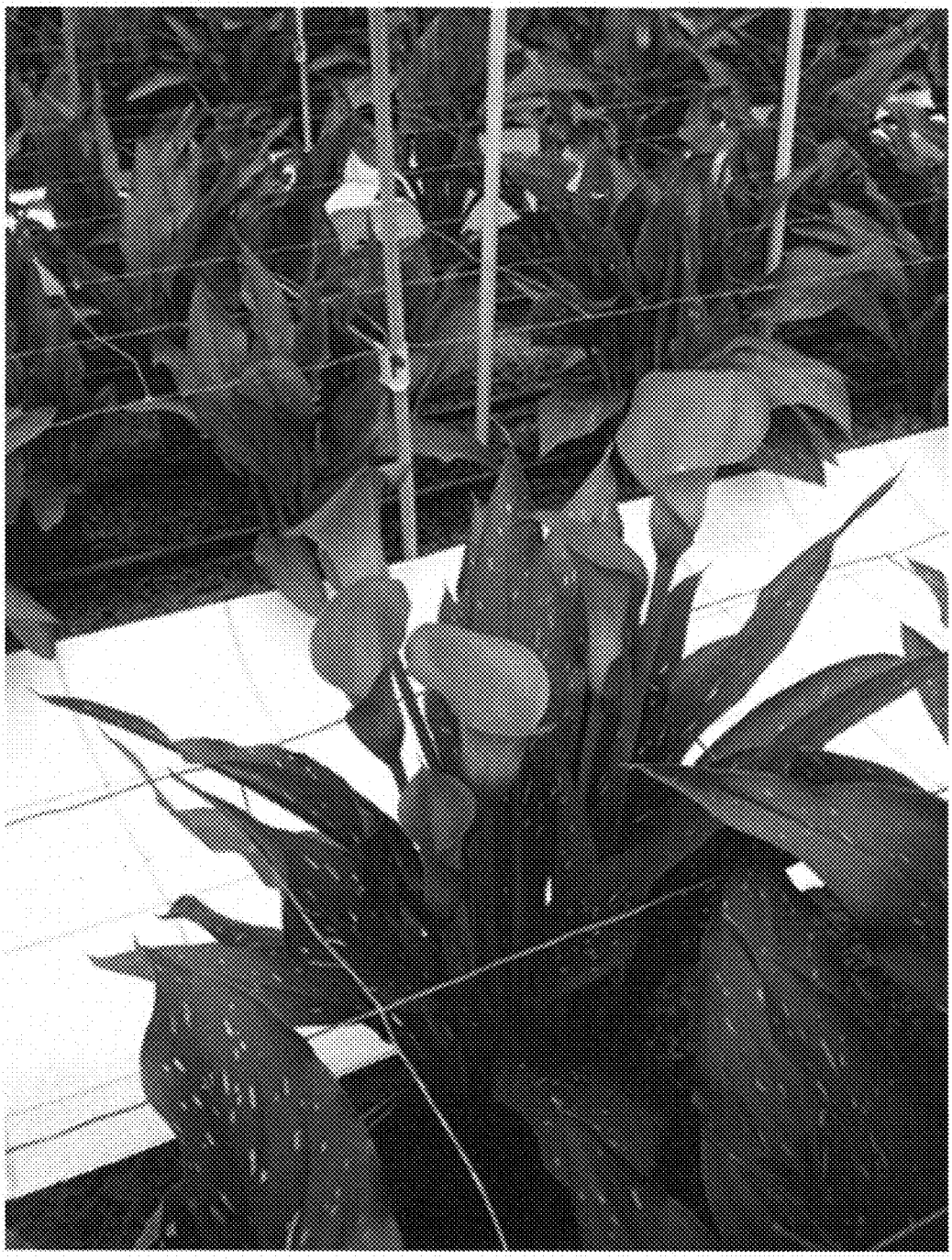
FIG. 1 is a photograph of a plant of the new variety.
Figure 2:
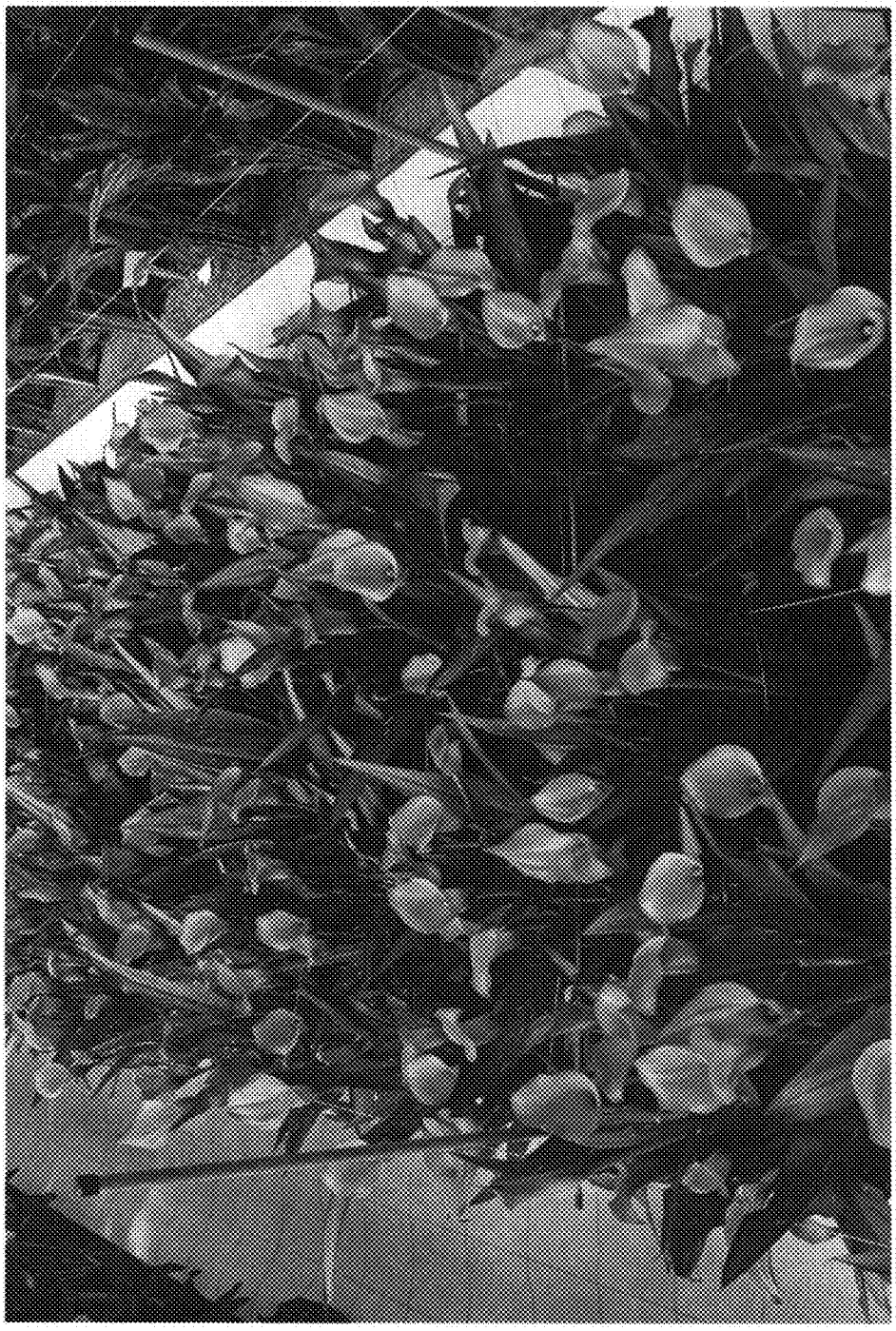
FIG. 2 is a photograph of a group of multiple plants of the new variety.

Size:
- *Height of the leaf canopy above the soil.*—10-40 cm.
- *Height of top of inflorescence above the soil.*—15-45 cm.
- *Diameter.*—15-50 cm.

Form: Erect.

Number of inflorescences per tuber:
- *Size* 14-16 *cm in diameter.*—4-10 inflorescences.
- *Size* 16-18 *cm in diameter.*—8-20 inflorescences.
- *Size* 18-20 *cm in diameter.*—8-25 inflorescences.

Branches:
- *Character.*—Many; like the variety 'Odessa' (U.S. Plant Pat. No. 18,833).
- *Color.*—Between Green Group RHS 143A and 143B.

Leaves:
- *Size.*—Width: 2-8 cm. Length: 7-30 cm.
- *Number per plant.*—20-30.
- *Shape.*—Lanceolate.
- *Color.*—Upper surface: Green Group RHS 137A to 137B. Lower surface: Green Group RHS 143A to 143B.
- *Margin.*—Undulate; having a color of Green Group RHS 137A to 137B.
- *Veins.*—Configuration: Pinnate. Color: Yellow-Green Group RHS 144A to 144B.
- *Surface quality.*—Leathery.
- *Petiole.*—Length: 5-25 cm. Color: The base is White Group RHS 155A, and the upper part is Yellow-Green Group RHS 144A to 144B.

Roots:
- *Color.*—White.
- *Branching.*—Similar to other *Zantedeschia* varieties.

The Inflorescence and Seeds

Spathe:
- *Size.*—Length (measured from opening to tip): 5-10 cm. Width: 3.5-6 cm. Height: 4-9 cm.
- *Color.*—Upper surface: Varies between Red-Purple Group RHS 58D and 60A. Lower surface: Varies between Yellow-Green Group RHS 144A and 144B.
- *Vein color.*—Between Red-Purple Group RHS 60A and 60B.
- *Shape.*—Cupped.

Spadix:
- *Size.*—Length: 15-40 mm. Diameter: 3-9 mm.
- *Color.*—Between Yellow-Orange Group RHS 14B and 14C.
- *Position relative to spathe.*—Upright.

Peduncle:
- *Size.*—Length: 10-35 cm. Diameter: 3-10 mm.
- *Color.*—The upper part is between Yellow-Green Group RHS 144A and 144B, and the lower part is Green-White Group RHS 157C.

Reproductive organs:
- *Location of female organs.*—Basal position of the spadix.
- *Location of male organs.*—Upper position of the spadix.
- *Perianth.*—Conspicuous.
- *Stamens.*—Presence: Not visible before pollen release. Number: More than 20. Pollen amount: Similar to 'Picasso' (U.S. Plant Pat. No 15,282). Color: Between White Group RHS 155A and 155B.
- *Anther.*—Shape: Round. Length: Less than 1 mm. Color: Between Yellow-Orange Group RHS 14B and 14C.
- *Filament.*—Length: Less than 1 mm. Color: Between White Group RHS 155A and 155B.
- *Pistils.*—Number: 15 to 30. Length beyond perianth: About 1 mm.
- *Stigma.*—Shape: Round. Size: Less than 1 mm.
- *Style.*—Length: Less than 1 mm. Color: Between Yellow-Orange Group RHS 14C and 14D.
- *Ovaries.*—Texture: Smooth. Length: Between 1 to 10 mm. Width: Between 1 to 10 mm. Color: Top color is between Red-Purple Group RHS 59C and Yellow-Green Group RHS 144D, bottom color is from White Group RHS 155B to Green-White Group RHS 157C.

Seeds:
- *Length.*—4-7 mm.
- *Width.*—3-6 mm.
- *Color.*—Between Yellow-Green Group RHS 150A and 151A.
- *Amount.*—Between 1-50.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July.

Lastingness: About two weeks on the plant.

Fragrance: None.

I claim:

1. A new and distinct variety of calla lily plant named 'Zazu' as herein described and illustrated.

* * * * *